United States Patent [19]

Hamasaki

[11] Patent Number: 6,022,658
[45] Date of Patent: Feb. 8, 2000

[54] NITRO GROUP-CONTAINING NAPHTHOQUINONE DERIVATIVES AND PHOTOSENSITIVE MATERIAL USING THE SAME FOR ELECTROPHOTOGRAPHY

[75] Inventor: Kazunari Hamasaki, Osaka, Japan

[73] Assignee: Mita Industrial Co Ltd., Osaka, Japan

[21] Appl. No.: 09/296,812

[22] Filed: Apr. 23, 1999

[30] Foreign Application Priority Data

May 1, 1998 [JP] Japan ................................. 10-122313

[51] Int. Cl.⁷ .............................. G03G 5/06; C07C 50/00
[52] U.S. Cl. .......................... 430/83; 552/299; 552/298
[58] Field of Search ............................................. 552/299

[56] References Cited

U.S. PATENT DOCUMENTS

| | | | |
|---|---|---|---|
| 4,634,654 | 1/1987 | Singer | 430/223 |
| 4,929,642 | 5/1990 | Lindner et al. | 514/510 |

OTHER PUBLICATIONS

Kang et al. (CA 113:115035 abstract of J. Chem. Soc., Perkin Trans. 1 (1990), (3), 441–5).
Grinev et al. (CA 55:8429f, CAOLD).

Primary Examiner—Jose' G. Dees
Assistant Examiner—Sabiha N. Qazi

[57] ABSTRACT

A nitro group-containing naphthoquinone derivative represented by the following general formula:

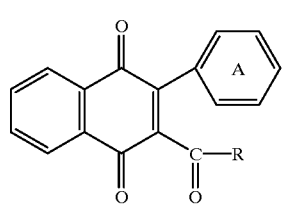

(1)

wherein R is a monovalent hydrocarbon group having a nitro group, and a ring A may be substituted with a substituent.

This compound is a novel substance and is useful as an electron-transporting agent for an electrophotosensitive material. The electrophotosensitive material using the electron-transporting agent is highly sensitive, exhibits favorable repetitive properties, and makes it possible to favorably form images for extended periods of time.

3 Claims, 1 Drawing Sheet

NITRO GROUP-CONTAINING NAPHTHOQUINONE DERIVATIVES AND PHOTOSENSITIVE MATERIAL USING THE SAME FOR ELECTROPHOTOGRAPHY

BACKGROUND OF THE INVENTION

1. Field of the Invention

The present invention relates to nitro group-containing naphthoquinone derivatives and to a photosensitive material for electrophotography which contains a nitro group-containing naphthoquinone derivative as an electron transporting agent and is used for the electrophotographic copy, printer and common paper facsimile.

2. Description of the Prior Art

In an electrophotographic method, an electrophotosensitive material is electrically charged and is exposed to image-bearing light to form an electrostatic latent image which is, then, developed into a toner image in a state where a developing bias voltage is applied, and the formed toner image is transferred onto a transfer paper or the like paper and is fixed to form an image. This electrophotographic method is extensively used for the digital or analog copy, printer and common paper facsimile.

A selenium photosensitive material and an amorphous silicon photosensitive material have heretofore been used for the electrophotography. In recent years, however, an organic photosensitive material (OPC) has also been extensively used. Representative examples of the organic photosensitive material include a laminated-layer photosensitive material of the separated function type in which a charge-generating agent (CGM) and a charge-transporting agent (CTM) are laminated one upon the other as separate layers, and a single-layer photosensitive material in which the CGM and the CTM are formed as a single dispersion layer.

As the charge-generating agent, there have been known a variety of inorganic or organic charge-generating agents such as selenium, selenium-tellurium, amorphous silicon, pyrylium salt, azo pigment, disazo pigment, trisazo pigment, anthanthrone pigment, phthalocyanine pigment, indigo pigment, threne pigment, toluidine pigment, pyrazoline pigment, pyranthrone pigment, perylene pigment and quinacridone pigment. As the charge-transporting agent, there have been known positive hole-transporting agents such as poly-N-vinylcarbazole, phenanthrene, N-ethylcarbazole, 2,5-diphenyl-1,3,4-oxadiazole, 2,5-bis-(4-diethylaminophenyl)-1,3,4-oxadiazole, bis-diethylaminophenyl-1,3,6-oxadiazole, 4,4'-bis(diethylamino)-2,2'-dimethyltriphenylmethane, 2,4,5-triaminophenylimidazole, 2,5-bis(4-diethylaminophenyl)-1,3,4-triazole, 1-phenyl-3-(4-diethylaminostyryl)-5-(4-diethylaminophenyl)-2-pyrazoline, p-diethylaminobenzaldehyde-(diphenylhydrazone), tetra(m-methylphenyl) methaphenylenediamine, N,N,N',N'-tetraphenylbenzidine derivative, N,N'-diphenyl-N,N'-dixylylbenzidine, as well as electron-transporting agents such as 2-nitro-9-fluorenone, 2,7-dinitro-9-fluorenone, 2,4,7-trinitro-9-fluorenone, 2,4,5,7-tetranitro-9-fluorenone, 2-nitrobenzothiophene, 2,4,8-trinitrothioxanthone, dinitroanthracene, dinitroacridine, dinitroanthraquinone, naphthoquinones, and 3,5-dimethyl-3',5'-di-t-butyldiphenoquinone.

Among the charge-transporting agents, however, very few electron-transporting agents satisfy a practicable level. Even the 3,5-dimethyl-3',5'-di-t-butyldiphenoquinone which has been regarded to exhibit excellent sensitivity, is not still satisfactory in regard to the sensitivity.

Thus, an electron-transporting agent that exhibits an increased degree of sensitivity has been demanded in the field of electrophotography.

SUMMARY OF THE INVENTION

The present inventors have conducted the study concerning the electron-transporting agent that exhibits an increased degree of sensitivity, have succeeded in synthesizing nitro group-containing naphthoquinone derivatives that will be described below in detail, and have discovered that the nitro group-containing naphthoquinone derivatives exhibit a very high sensitivity when they are contained in a photosensitive material.

That is, the object of the present invention is to provide nitro group-containing naphthoquinone derivatives that are useful as an electron-transporting agent.

Another object of the present invention is to provide an organic photosensitive material for electrophotography containing a novel electron-transporting agent and having a high photosensitivity and a low residual potential and, as a result, capable of stably forming a highly dense vivid image without background fogging for extended periods of time.

According to the present invention, there is provided a nitro group-containing naphthoquinone derivative represented by the general formula (1):

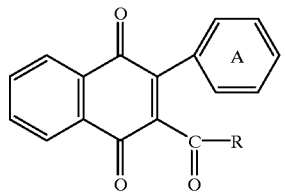

(1)

wherein R is a monovalent hydrocarbon group having a nitro group, and a ring A may be substituted with a substituent.

According to the present invention, furthermore, there is provided a photosensitive material for electrophotography containing the above-mentioned nitro group-containing naphthoquinone derivative.

It is further desired that the elecrophotosensitive material further contains an electron acceptor in addition to the above-mentioned nitro group-containing naphthoquinone derivative.

DETAILED DESCRIPTION OF THE INVENTION

Figure 1:
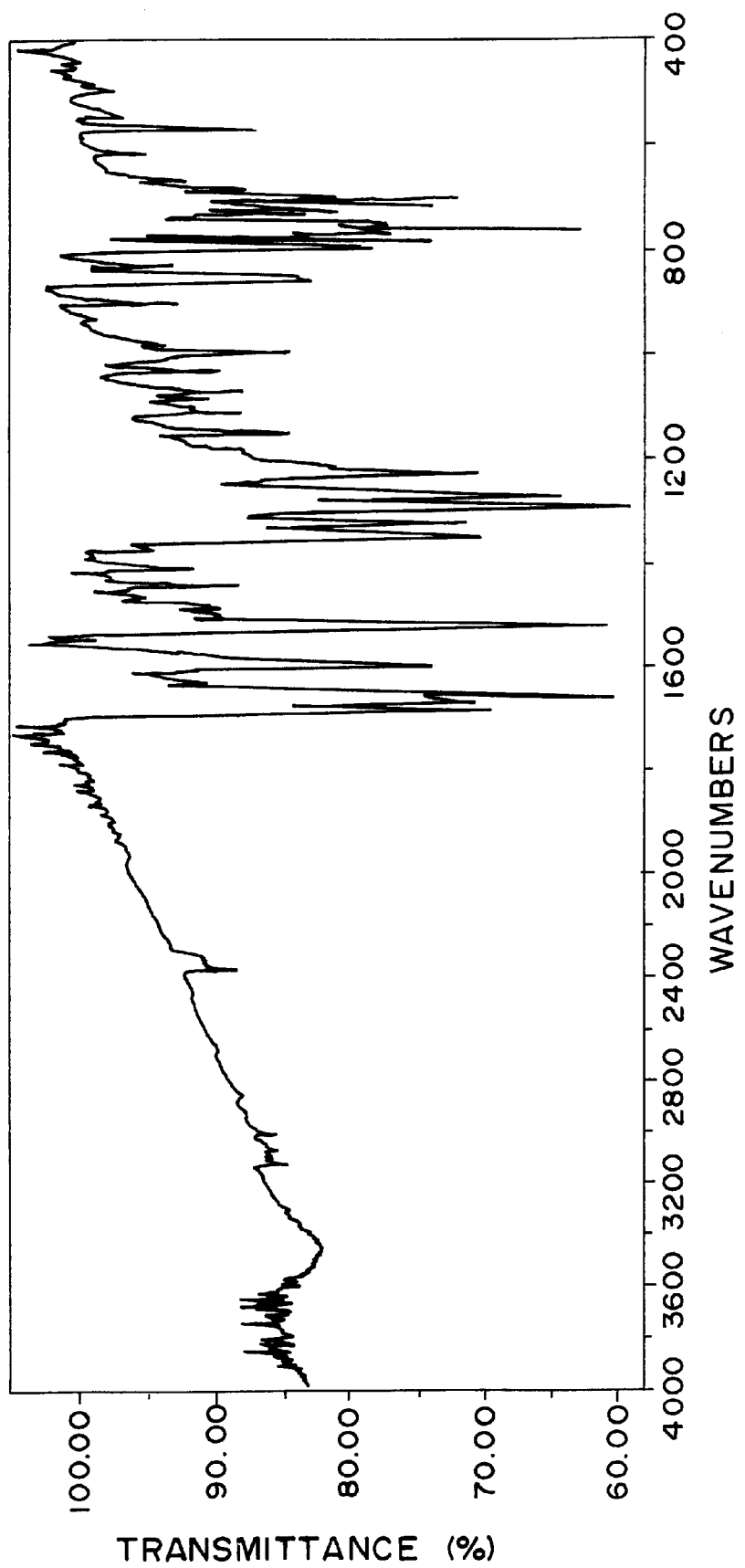
FIG. 1 shows an infrared-ray absorption spectrum of a nitro group-containing naphthoquinone derivative (2-phenyl-3-(p-nitrobenzoyl)-1,4-naphthoquinone) synthesized according to a synthesis example that will be described later.

A nitro group-containing naphthoquinone derivative of the present invention has a structural feature in that it has a phenyl group at the second position of a 1,4-naphthoquinone skeleton and a hydrocarbon carbonyl group at the third position, a monovalent hydrocarbon group bonded to the carbonyl group at the third position having a nitro group as represented by the above-mentioned formula (1).

Reference should be made to Experimental Example 1 appearing later. That is, in Experimental Example 1, an index of photosensitivity is represented by an after-the-exposure-to-light potential after a photosensitive material containing a charge-generating agent and an electron-transporting agent is irradiated with a beam of a predetermined intensity for a predetermined period of time (the smaller the potential, the higher the sensitivity). The nitro group-containing naphthoquinone derivatives (Examples 1 to 9) of the above-mentioned formula (1) exhibit considerably lower after-the-exposure-to-light potentials than that of the 3,5-dimethyl-3',5'-di-t-butyl- 4,4'-diphenoquinone (Comparative Examples 10, 11, 13, 14 and 16) which has been regarded to exhibit the highest sensitivity as an electron-transporting agent and, thus, exhibit excellent photosensitivities.

The nitro group-containing naphthoquinone derivatives exhibit low after-the-exposure-to-light potentials even compared with the compounds having similar chemical structures but without containing nitro group (Comparative Examples 1 to 5), and exhibit excellent photosensitivities.

The compound without containing nitro group used in Comparative Example 1 exhibits a considerably improved sensitivity and a considerably low after-the-exposure-to-light potential (Comparative Examples 6 to 9) when it is used in combination with an electron acceptor. However, an electrophotosensitive material containing the above compound and the electron acceptor exhibits low repetitive properties as demonstrated by Experimental Example 2 appearing later, and exhibits a markedly dropped charged potential after the charge-discharge process is repeated about 500 times. On the other hand, the electrophotosensitive material containing the nitro group-containing naphthoquinone derivative of the present invention exhibits very favorable repetitive properties, and maintains a charged potential which is equal to that of the initial time even after the charge-discharge process is repeated about 500 times, making it possible to favorably form images over extended periods of time.

Furthermore, the photosensitive material of the present invention exhibits a low residual potential after the exposure to light and makes it possible not only to form a charge image of a high contrast but also to stably form images with little background fogging for extended periods of time without disadvantage that is caused by the accumulation of electric charge.

[Nitro Group-Containing Naphthoquinone Derivatives]

The nitro group-containing naphthoquinone derivative used in the present invention has a chemical structure expressed by the following formula (2)(which is substantially the same as the above-mentioned formula (1)),

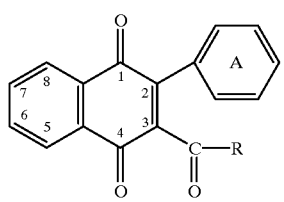

(2)

This naphthoquinone derivative has a feature in the chemical structure in that it has a quinoid carbon atom at the first and fourth positions of the naphthalene ring, has a phenyl group at the second position which is a neighboring carbon atom, and has a nitro group-containing monovalent hydrocarbon group bonded to the third position via a carbonyl group. It is believed that owing to this feature in the structure, the naphthoquinone derivative contains many conjugated π-electrons which contribute to increasing the light absorption efficiency and the electron-transporting ability.

The above-mentioned group R is a monovalent hydrocarbon group in which some hydrogen atoms are substituted with the nitro groups. Examples of the monovalent hydrocarbon group to be substituted with the nitro groups include alkyl groups having 1 to 10 carbon atoms, such as methyl group, ethyl group, n-propyl group, iso-propyl group, n-butyl group, iso-butyl group, t-butyl group, amyl group, and 2-ethylhexyl group; alkenyl groups having 2 to 10 carbon atoms such as vinyl group, and allyl group; cycloalkyl groups having 3 to 6 carbon atoms such as cyclohexyl group, and cyclopentyl group; cycloalkenyl groups having 5 to 6 carbon atoms such as cyclohexenyl group and the like group; aryl groups having 6 to 10 carbon atoms such as phenyl group, tolyl group, xylyl group, ethylphenyl group, and naphthyl group; aralkyl groups having 7 to 9 carbon atoms such as benzyl group, phenetyl group and cumyl group. Among these hydrocarbon groups, an aryl group and, particularly, a phenyl group is preferred.

It is essential that some hydrogen atoms of the monovalent hydrocarbon group are substituted with the nitro groups. The number of the nitro groups is at least one, and its number is permitted up to three. In many cases, however, the nitro group of a number of one suffices. When the hydrocarbon group is a phenyl group, it is generally desired that the nitro group is bonded to the p-position. The nitro group, however, may be bonded to the ortho position.

The phenyl group (A) present at the second position may not be substituted or may be substituted with a substituent. Suitable examples of the substituent include a lower alkyl group, a lower alkoxyl group and a halogen atom.

It is desired that the number of the substituents is not larger than 2 and, particularly, not larger than 1.

Concrete examples of the nitro group-containing naphthoquinone derivative are as follows:
2-phenyl-3-(p-nitrobenzoyl)-1,4-naphtoquinone,
2-phenyl-3- (β-nitropropionyl) -1, 4-naphthoquinone,
2-(p-toluyl)-3-(p-nitrobenzoyl)-1,4-naphthoquinone,
2-phenyl-3-(o,p-dinitrobenzoyl)-1,4-naphthoquinone.

The dinaphthoquinones used in the present invention are not limited to the above-mentioned examples only as a matter of course. Among them, the 2-phenyl-3-(p-nitrobenzoyl)-1,4-naphthoquinone is preferred.

The above-mentioned naphthoquinone derivative is produced by reacting a 1,3-diketo-2-phenylhydroindene represented by the following formula (3),

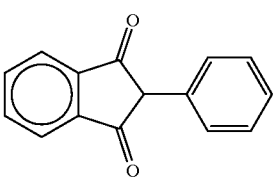

(3)

with a bromide represented by the following formula (4)

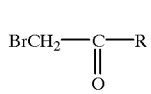

(4)

in the presence of a sodium hydride to prepare a 1,3-diketo-2-phenyl-2-nitro-substituted hydrocarbon carbonylmethyl-hydroindene represented by the following formula (5),

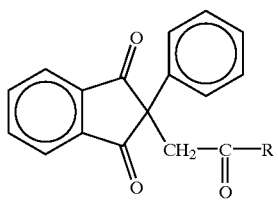
(5)

producing a 2-phenyl-3-nitro-substituted hydrocarbon carbonyl-1,4-dinaphthol represented by the following formula (6),

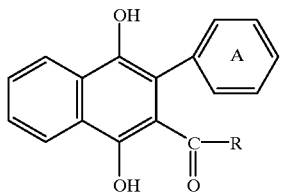
(6)

by the arrangement of the compound of the formula (5) in the presence of a sodium hydride, followed by the oxidation with chloroanil or the like thereby to obtain the compound of the above-mentioned formula (1),

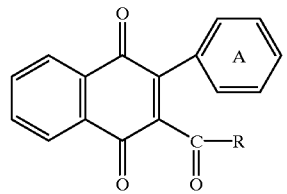
(1)

[Electrophotosensitive Materials]

The electrophotosensitive material of the present invention may be any photosensitive material provided it contains the above-mentioned naphthoquinone derivative as an electron-transporting agent and may, for example, be a single dispersion-type photosensitive material containing the electron-transporting agent (ETM) and the charge-generating agent (CGM) in a single photosensitive layer or a laminated-layer photosensitive material having the charge-generating layer (CGL) and the charge-transporting layer (CTL).

The composition of the photosensitive material will now be described.

(1) Charge-Generating Agents

As the charge-generating agent, there can be used, for example, selenium, selenium-tellurium, amorphous silicon, pyrylium salt, azo pigment, disazo pigment, anthanthrone pigment, phthalocyanine pigment, indigo pigment, threne pigment, toluidine pigment, pyrazoline pigment, perylene pigment and quinacridone pigment in one kind or in two or more kinds being mixed together so as to exhibit an absorption wavelength in a desired region.

The following phthalocyanine pigment, perylene pigment and bisazo pigment can be particularly preferably used.

Phthalocyanine pigment such as metal-free phthalocyanine, aluminum phthalocyanine, vanadium phthalocyanine, cadmium phthalocyanine, antimony phthalocyanine, chromium phthalocyanine, copper 4-phthalocyanine, germanium phthalocyanine, iron phthalocyanine, chloroaluminum phthalocyanine, oxotitanyl phthalocyanine, chloroindium phthalocyanine, chlorogallium phthalocyanine, magnesium phthalocyanine, dialkyl phthalocyanine, tetramethyl phthalocyanine, and tetraphenyl phthalocyanine. The crystalline form may be any one of α-type, β-type, γ-type, δ-type, ε-type, σ-type, χ-type or τ-type.

Perylene pigment represented by the general formula (7)

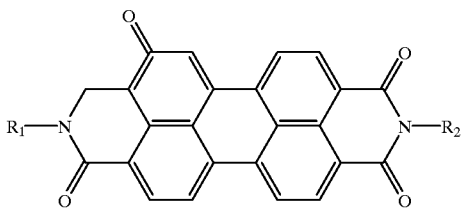
(7)

wherein R1 and R2 are each a substituted or unsubstituted alkyl group having not more than 18 carbon atoms, cycloalkyl group, aryl group, alkaryl group or aralkyl group.

Examples of the alkyl group include ethyl group, propyl group, butyl group and 2-ethylhexyl group, examples of the cycloalkyl group include cyclohexyl group and the like group, examples of the aryl group include phenyl group, naphthyl group, examples of the alkaryl group include tolyl group, xylyl group, ethylphenyl group, and examples of the aralkyl group include benzyl group and phenetyl group. Examples of the substituent include alkoxyl group and halogen atom.

Bisazo pigment represented by the following formula (8),

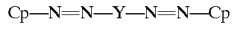
(8)

wherein Y is a divalent aromatic group that may include a heterocyclic group, and Cp is a coupler residue.

As the divalent aromatic group, there can be exemplified benzene, naphthalene, anthracene, phenanthrene, chrysene, anthraquinone, biphenyl, bisphenols, and a divalent group derived from a heterocyclic ring or a combination thereof. As the heterocyclic group, there can be exemplified monocyclic or polycyclic saturated or unsaturated heterocyclic rings having nitrogen, oxygen, sulfur or a combination thereof in the ring. Concrete examples include pyrrole, pyrazole, thiophene, furan, imidazoline, pyrimidine, pyrazoline, pyran, pyridine, benzofuran, benzoimidazoline, benzoxazole, indoline, quinoline, chromene, carbazole, dibenzofuran, xanthene and thioxanthene. These divalent groups may no be substituted or substituted. As the substituent, there can be exemplified alkyl group, aryl group and heterocyclic group. Here, examples of the alkyl group include methyl group, ethyl group, propyl group, butyl group and amyl group; examples of the aryl group include phenyl group, naphthyl group, biphenyl group, anthrile group, phenanthrile group and fluorenyl group; and examples of the substituted heterocyclic group include a monocyclic or polycyclic saturated or unsaturated heterocyclic group containing nitrogen, oxygen, sulfur or a combination thereof in the ring, such as thienyl group, furyl group, imidazolyl group, pyrrolyl group, pyrimidinyl group, imidazole group, pyradinyl group, pyrazolynyl group, pyrrolidinyl group, pyranyl group, piperidyl group, piperazinyl group, morpholyl group, pyridyl group, pyrimidyl group, pyrrolidinyl group, pyrrolinyl group, benzofuryl group, benzimidazolyl group, benzofuranyl group, indolyl group, quinolyl group, carbazolyl group and dibenzofuranyl group.

As the coupler residue in the formula (8), there can be used any residue of the coupler (azo coupling component) used for the azo pigment of this kind, such as substituted or unsubstituted phenols, naphthols or a hydroxyl group-containing heterocyclic ring compound. Here, as the substituent, there can be exemplified lower alkyl group, lower alkoxyl group, aryl group, acyloxyl group, halogen atom such as chloro, hydroxyl group, nitryl group, nitro group, amino group, amide group, acyloxyl group and carboxyl group.

(2) Charge-Transporting Agents

The charge-transporting agent used in the present invention contains the above-mentioned nitro group-containing naphthoquinone derivative as an electron-transporting agent. The nitro group-containing naphthoquinone derivative can be used alone as a charge-transporting agent, and can be further used in combination with a positive hole-transporting agent or an electron acceptor. The use in combination makes it possible to further enhance the photosensitivity.

As the positive hole-transporting material, the following compounds have been known and those that exhibit excellent solubility and positive hole-transporting property are selected out of them.
Pyrene,
N-ethylcarbazole,
N-isopropylcarbazole,
N-methyl-N-phenylhydrazino-3-methylindene-9-carbazole,
N,N-diphenylhydrazino-3-methylindene-9-ethylcarbazole,
N,N-diphenylhydrazino-3-methylindene-10-ethylphenothiazine,
N,N-diphenylhydrazino-3-methylindene-10-ethylphenoxazine,
p-diethylaminobenzaldehyde-N,N-diphenylhydrazone,
p-diethylaminobenzaldehyde-α-naphthyl-N-phenylhydrazone,
p-pyrrolidinobenzaldehyde-N,N-diphenylhydrazone,
1,3,3-trimethylindolenine-ω-aldehyde-N,N-diphenylhydrazone,
p-diethylbenzaldehyde-3-methylbenzthiazolinone-2-hydrazone,
2,5-bis(p-diethylaminophenyl)-1,3,4-oxadiazole,
1-phenyl-3-(p-diethylaminostyryl)-5-(p-diethylaminophenyl)pyrazoline,
1-[quinonyl(2)]-3-(p-diethylaminostyryl)-5-(p-diethylaminophenyl)pyrazoline,
1-[pyridyl(2)]-3-(p-diethylaminostyryl)-5-(p-diethylaminophenyl)pyrazoline,
1-[6-methoxy-pyridyl(2)]-3-(p-diethylaminostyryl)-5-(p-diethylaminophenyl)pyrazoline,
1-[pyridyl(3)]-3-(p-diethylaminostyryl)-5-(p-diethylaminophenyl)pyrazoline1-[lepidyl(3)]-3-(p-diethylaminostyryl)-5-(p-diethylaminophenyl)pyrazoline,
1-[pyridyl(2)]-3-(p-diethylaminostyryl)-4-methyl-5-(p-diethylaminophenyl)pyrazoline,
1-[pyridyl(2)]-3-(α-methyl-p-diethylaminostyryl)-3-(p-diethylaminophenyl)pyrazoline,
1-phenyl-3-(p-diethylaminostyryl)-4-methyl-5-(p-diethylaminophenyl)pyrazoline, spiropyrazoline,
2-(p-diethylaminostyryl)-3-diethylaminobenzoxazole,
2-(p-diethylaminophenyl)-4-(p-dimethylaminophenyl)-5-(2-chlorophenyl)oxazole,
2-(p-diethylaminostyryl)-6-diethylaminobenzothiazole,
bis(4-diethylamino-2-methylphenyl)phenylmethane,
1,1-bis(4-N,N-diethylamino-2-methylphenyl)heptane,
1,1,2,2-tetrakis(4-N,N-dimethylamino-2-methylphenyl)ethane,
N,N'-diphenyl-N,N'-bis(methylphenyl)benzidine,
N,N'-diphenyl-N,N'-bis(ethylphenyl)benzidine,
N,N'-diphenyl-N,N'-bis(propylphenyl)benzidine,
N,N'-diphenyl-N,N'-bis(butylphenyl)benzidine,
N,N'-bis(isopropylphenyl)benzidine,
N,N'-diphenyl-N,N'-bis(secondary butylphenyl)benzidine,
N,N'-diphenyl-N,N'-bis(tertiary butylphenyl)benzidine,
N,N'-diphenyl-N,N'-bis(2,4-dimethylphenyl)benzidine,
N N'-diphenyl-N,N'-bis(chlorophenyl)benzidine,
triphenylamine,
poly-N-vinylcarbazole,
polyvinyl pyrene,
polyvinyl anthracene,
polyvinyl acridine,
poly-9-vinylphenyl anthracene,
pyrene-formaldehyde resin, and
ethylcarbazole formaldehyde resin.

As a preferred positive hole-transporting agent, there can be exemplified aromatic amines represented by the following formula (9),

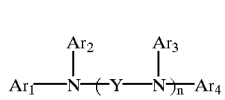

(9)

wherein Ar1, Ar2, Ar3 and Ar4 are substituted or unsubstituted aryl groups, Y is a substituted or unsubstituted arylene group, and n is a number of zero or 1.

As another preferred positive hole-transporting agent, there can be exemplified hydrazones and, particularly, hydrazones represented by the following formula (10),

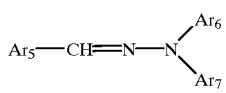

(10)

wherein Ar5, Ar6 and Ar7 are substituted or unsubstituted aryl groups.

As the electron acceptor used in combination with the nitro group-containing naphthoquinone derivative (electron-transporting agent) of the present invention, there can be used any one that has heretofore been used as the electron-transporting agent and, particularly, benzoquinones or naphthoquinones represented by the following formula (11),

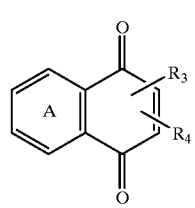

(11)

wherein a condensed ring A may be omitted, and R3 and R4 are hydrogen atoms, alkyl groups or acyloxyl groups, such as p-benzoquinone, 2,6-t-butylbenzoquinone, 1,4-naphthoquinone, 2-t-butyl-3-benzoyl-1,4-naphthoquinone, or 2-phenyl-3-benzoyl-1,4-naphthoquinone, and diphenoquinones represented by the following formula (12),

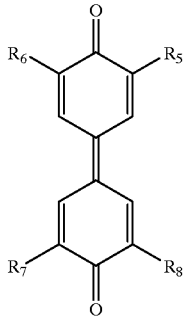

(12)

wherein R5, R6, R7 and R8 are alkyl groups, cycloalkyl groups, aryl groups or alkoxyl groups, which may be the same or different
such as 3,5-dimethyl-3',5'-di-t-butyldiphenoquinone, 3,5-dimethoxy-3',5'-di-t-butyldiphenoquinone, 3,3'-dimethyl-5,5'-di-t-butyldiphenoquinone, 3,5'-dimethyl-3',5-di-t-butyldiphenoquinone, 3,5,3',5'-tetramethyldiphenoquinone, 2,6,2',6'-tetra-t-butyldiphenoquinone, 3,5,3',5'-tetraphenyldiphenoquinone, or 3,5,3',5'-tetracyclohexyldiphenoquinone.

(3) Binder Resins

As a resin medium for dispersing the charge-generating agent and the charge-transporting agent, there can be used a variety kinds of resins such as olefin polymers like styrene polymer, acrylic polymer, styrene-acrylic polymer, ethylene-vinyl acetate copolymer, polypropylene, and ionomer, and a variety kinds of polymers such as polyvinyl chloride, vinyl chloride-vinyl acetate copolymer, polyester, alkyd resin, polyamide, polyurethane, epoxy resin, polycarbonate, polyarylate, polysulfone, diallyl phthalate resin, silicone resin, ketone resin, polyvinyl butyral resin, polyether resin, phenol resin and photo-curing resins like epoxy acrylate. These binder resins can be used in one kind or in two or more kinds being mixed together. Preferred resins include styrene polymer, acrylic polymer, styrene-acrylic polymer, polyester resin, alkyd resin, polycarbonate and polyarylate.

Particularly preferred resins are a polycarbonate, Panlite manufactured by Teijin Kasei Co., PCZ manufactured by Mitsubishi Gas Kagaku Co., that pertain to a polycarbonate derived from bisphenols and phosgene, the polycarbonate is represented by the following general formula (13),

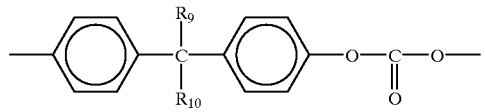

(13)

wherein R9 and R10 are hydrogen atoms or lower alkyl groups, and R9 and R10 being coupled together may form a cyclo ring such as a cyclohexane ring together with a carbon atom that is bonded thereto.
[Single-Layer Photosensitive Materials]

In the single-layer photosensitive material, the charge-generating agent is blended in an amount of from 0.1 to 50 parts by weight and, preferably, from 0.5 to 30 parts by weight, and the electron-transporting agent is blended in an amount of from 5 to 100 parts by weight and, preferably, from 10 to 80 parts by weight per 100 parts by weight of the binder resin. The positive hole-transporting agent is blended in an amount of from 5 to 500 parts by weight and, preferably, from 25 to 200 parts by weight. It is further desired that the total amount of the positive hole-transporting agent and the electron-transporting agent is from 20 to 500 parts by weight and, preferably, from 30 to 200 parts by weight per 100 parts by weight of the binder resin. When the electron-accepting compound is to be contained in the single-layer photosensitive material, it is desired that the electron-accepting compound is blended in an amount of from 0.1 to 40 parts by weight and, preferably, from 0.5 to 20 parts by weight per 100 parts by weight of the binder resin.

In the case of a single-layer photosensitive material, the thickness of the photosensitive layer is usually selected to be from 5 to 100 μm and, particularly, from 10 to 50 μm from the standpoint of electrophotographic properties.
[Laminated-Layer Photosensitive Materials]

In the case of the laminated-layer photosensitive material, it is desired that the charge-generating agent (CGM) is contained in an amount of from 5 to 1000 parts by weight and, particularly, from 30 to 500 parts by weight per 100 parts by weight of the solid resin component in the charge-generating layer (CGL) and that the dinaphthoquinone electron-transporting agent is contained in an amount of from 0.5 to 50 parts by weight and, particularly, from 1 to 40 parts by weight per 100 parts by weight of the solid resin component in the charge-transporting layer (CTL).

In the case of the substrate/CGL/CTL photosensitive material, it is desired that the CGL lies over a range of, usually, from 0.01 to 5 μm and, particularly, from 0.1 to 3 μm and that the CTL lies over a range of from 2 to 100 μm and, particularly, from 5 to 50 μm.
[Preparation of the Photosensitive Materials]

The composition for forming the photosensitive material used in the present invention can be blended with various blending agents that have been known per se, such as antioxidant, radical-trapping agent, singlet quencher, UV-absorbing agent, softening agent, surface-reforming agent, defoaming agent, filler, viscosity-imparting agent, dispersion stabilizer, wax, acceptor and donor within a range in which they will not adversely affect the electrophotographic properties.

Upon blending at least the upper layer in the photosensitive material with a steric hindrant phenolic antioxidant in an amount of from 0.1 to 50% by weight per the total solid components, furthermore, the durability of the photosensitive material can be markedly improved without adversely affecting the electrophotographic properties.

As the electrically conducting substrate on which the photosensitive layer will be formed, there can be used various materials having electrically conducting property like a simple substance of a metal, such as aluminum, copper, tin, platinum, gold, silver, vanadium, molybdenum, chromium, cadmium, titanium, nickel, indium, stainless steel or brass, or a plastic material on which the above-mentioned metals are deposited or laminated, or a glass coated with aluminum iodide, tin oxide, or indium oxide. The photosensitive material of the present invention preferably employs an ordinary aluminum blank tube and, particularly, an aluminum blank tube coated with an alumite film maintaining a thickness of from 1 to 50 μm.

To form the photosensitive material, the charge-generating agent, electron-transporting agent and binder resin are used in combination, or the charge-generating agent and binder resin are used in combination, or the electron-transporting agent and binder resin are used in combination, thereby to prepare a coating composition relying upon a widely known method such as using a roll mill, ball mill, Atritor, paint shaker or ultrasonic dispersing device, and the coating composition is applied relying on a known coating means and is, as required, laminated followed by drying.

A variety of organic solvents can be used for forming a coating solution. Examples include alcohols such as methanol, ethanol, isopropanol and butanol; aliphatic hydrocarbons such as n-hexane, octane, and cyclohexane; aromatic hydrocarbons such as benzene, toluene and xylene; halogenated hydrocarbons such as dichloromethane, dichloroethane, carbon tetrachloride and chlorobenzene; ethers such as dimethyl ether, diethyl ether, tetrahydrofurane, ethylene glycol dimethyl ether, and diethylene glycol dimethyl ether; ketones such as acetone, methyl ethyl ketone and cyclohexanone; esters such as ethyl acetate and methyl acetate; and dimethylformamide and dimethylsulfoxide, which can be used in one kind or in two or more kinds being mixed together. The concentration of solid components in the coating solution is usually from 5 to 50%.

There is no particular limitation on the method of forming images by using the electrophotosensitive material of the present invention. Generally, the photosensitive material is electrically charged uniformly and is exposed to image-bearing light to form an electrostatic latent image. The electrostatic latent image is then developed by using a nonmagnetic one-component toner, a magnetic one-component toner, a magnetic two-component developing agent or a nonmagnetic two-component developing agent. The developed image is then transferred onto a transfer paper and is fixed thereby to form an image.

The present invention will now be described by way of Examples.

SYNTHESIS EXAMPLE

Method of synthesizing a 2-phenyl-3-(p-nitrobenzoyl)-1,4-naphthoquinone (hereinafter referred to as electron-transporting agent (i)).

10 Grams (0.045 mols) of a 1,3-diketo-2-phenylhydroindene and 1.3 g (0.054 mols) of NaH were introduced into an ice-cooled and argon-substituted two-way flask, and to which was slowly and dropwisely added 100 ml of THF. The mixture was stirred for a while until hydrogen evolved no longer. Then, 12.1 g (0.05 mols) of a p-nitrobenzoylmethane bromide was added thereto and was refluxed for 4 hours. After the reaction, the HCL water was added, and the reaction product was extracted with chloroform and an oil layer was dried with sodium sulfate. Thereafter, the solvent was distilled off under a reduced pressure to obtain a crude 1,3-diketo-2-phenyl-2-(p-nitrobenzoylmethyl)hydroindene.

The crude 1,3-diketo-2-phenyl-2-(p-nitrobenzoylmethyl) hydroindene and 1.3 g (0.054 mols) of NaH were introduced into the ice-cooled and argon-substituted two-way flask, and to which was slowly and dropwisely added 100 ml of THF. The mixture was refluxed for 6 hours.

After the reaction, the HCL water was added, and the reaction product was extracted with chloroform and an oil layer was dried with sodium sulfate. Then, 13 g (0.05 mols) of chloranil was added thereto, and the mixture was stirred at room temperature for 12 hours. After the reaction, an excess of chloranil was separated by filtration and the solvent was distilled off under a reduced pressure. Then, the reaction product was refined through the column chromatography (chloroform) and was further recrystallized with chloroform/ethanol to obtain 9.13 g of a yellow solid of a 2-phenyl-3-(p-nitrobenzoyl)-1,4-naphthoquinone (yield, 53%). The 2-phenyl-3-(p-nitrobenzoyl)-1,4-naphthoquinone exhibited a melting point of from 161 to 163° C. and infrared-ray absorption spectrum as shown in a chart of FIG. 1.

EXPERIMENTAL EXAMPLE 1

[Examples 1 to 9 and Comparative Examples 1 to 16]

In these Examples, the above-mentioned electron-transporting agent (i) was used as the electron-transporting agent.

In Comparative Examples 1 to 9, the following electron-transporting agent (ii) was used.

2-Phenyl-3-(benzoyl)-1,4-naphthoquinone (electron-transporting agent (ii)).

1. Preparation of Photosensitive Material.

(Single-Layer Photosensitive Material)

5 Parts by weight of a pigment shown in Table 1 as a charge-generating agent, 50 parts by weight of a compound shown in Table 1 as a positive hole-transporting agent, 30 parts by weight of a compound shown in Table 1 as an electron-transporting agent, 100 parts by weight of a polycarbonate as a binder agent, and 800 parts by weight of a tetrahydrofuran as a solvent, were mixed and dispersed by using a ball mill for 50 hours to prepare a coating solution for forming a single-layer photosensitive layer. The thus prepared solution was then applied onto an aluminum blank tube and was dried with the hot air heated at 100° C. for 60 minutes to obtain a single-layer photosensitive material for electrophotography having a film thickness of from 15 to 20 $\mu$m.

(Laminated-Layer Photosensitive Material)

100 Parts by weight of a charge-generating agent, 100 parts by weight of a binder resin (polyvinyl butyral) and 2000 parts by weight of a solvent (tetrahydrofuran) were mixed and dispersed by the ball mill for 50 hours to prepare a coating solution for forming a charge-generating layer. The coating solution was then applied onto an aluminum blank tube and was dried with the hot air heated at 100° C. for 60 minutes to prepare a charge-generating layer having a film thickness of 1 $\mu$m.

Furthermore, 100 parts by weight of an electron-transporting agent, 100 parts by weight of a polycarbonate and 800 parts by weight of a solvent (toluene) were mixed and dispersed by using the ball mill for 50 hours to prepare a coating solution for forming a charge-transporting layer. The coating solution was then applied onto the charge-generating layer, and was dried with the hot air heated at 100° C. for 60 minutes to form a charge-transporting layer having a film thickness of 20 $\mu$m thereby to obtain a laminated-layer photosensitive material.

2. Evaluation.

(1) Method of Evaluating the Photosensitivity (in the case of a phthalocyanine pigment).

By using a drum sensitivity tester, a voltage was applied to the photosensitive materials obtained in Examples and in Comparative Examples to electrically charge them up to +700 V. Then, the photosensitive materials were irradiated on their surfaces with monochromatic light of 780 nm (half-value width, 20 nm) through a band-pass filter for a predetermined period of time, and the degrees of attenuation of the potential were observed to measure the electrophotographic properties.

Source of light: halogen lamp
Intensity of light: 16 µW/cm² (780 nm)
Irradiation time: 80 msec
Measurement of potential after exposed to light: 330 msec after the start of the exposure to light The results were as shown in Table 1.

In Table 1, the column Vr (V) shows surface potentials of the photosensitive materials 330 milliseconds after the start of the exposure to light.

(2) Method of Evaluating the Photosensitivity (in the case of a perylene pigment).

By using a drum sensitivity tester, a voltage was applied to the photosensitive materials obtained in Examples and in Comparative Examples to electrically charge them up to +700 V. Then, the photosensitive materials were irradiated on their surfaces with white light from a halogen lamp for a predetermined period of time, and the degrees of attenuation of the potential were observed to measure the electrophotographic properties.

Source of light: halogen lamp
Intensity of light: 147 µW/cm²
Irradiation time: 50 msec
Measurement of potential after exposed to light: 330 msec after the start of the exposure to light The results were as shown in Table 1.

In Table 1, the column Vr (V) shows surface potentials of the photosensitive materials 330 milliseconds after the start of the exposure to light.

TABLE 1

| | Charge-gen agent | Positive hole-trans agent | Electron-trans agent | Electron acceptor | Vr (V) |
|---|---|---|---|---|---|
| Ex. 1 | PcH₂ | yes | (i) | — | 177 |
| Ex. 2 | PcTiO | yes | (i) | — | 200 |
| *Ex. 3 | PcH₂ | no | (i) | — | 279 |
| Ex. 4 | perylene | yes | (i) | — | 215 |
| *Ex. 5 | perylene | no | (i) | — | 298 |
| Ex. 6 | PcH₂ | yes | (i) | a | 130 |
| Ex. 7 | PcH₂ | yes | (i) | b | 125 |
| Ex. 8 | PcH₂ | yes | (i) | c | 122 |
| Ex. 9 | PcH₂ | yes | (i) | d | 119 |
| C. Ex. 1 | PcH₂ | yes | (ii) | — | 185 |
| C. Ex. 2 | PcTiO | yes | (ii) | — | 205 |
| *C. Ex. 3 | PcH₂ | no | (ii) | — | 285 |
| C. Ex. 4 | perylene | yes | (ii) | — | 225 |
| *C. Ex. 5 | perylene | no | (ii) | — | 310 |
| C. Ex. 6 | PcH₂ | yes | (ii) | a | 142 |
| C. Ex. 7 | PcH₂ | yes | (ii) | b | 138 |
| C. Ex. 8 | PcH₂ | yes | (ii) | c | 136 |
| C. Ex. 9 | PcH₂ | yes | (ii) | d | 133 |
| C. Ex. 10 | PcH₂ | yes | c | — | 220 |
| C. Ex. 11 | PcTiO | yes | c | — | 242 |
| C. Ex. 12 | PcH₂ | yes | — | — | 478 |
| *C. Ex. 13 | PcH₂ | no | c | — | 346 |
| C. Ex. 14 | perylene | yes | c | — | 294 |
| C. Ex. 15 | perylene | yes | — | — | 521 |
| *C. Ex. 16 | perylene | no | c | — | 386 | notes: in the Examples and the Comparative Examples added the mark (*), the laminated photosensitive materials are used.

PCH₂: metal-free phthalocyanine
PcTiO: oxotitanyl phthalocyanine
a: p-benzoquinone
b: 2,6-di-t-butylbenzoquinone
c: 3,5-dimethyl-3',5'-di-t-butyl-4,4'-diphenoquinone
d: 3,3',5,5'-tetra-t-butyl-4,4'-diphenoquinone
(i): 2-phenyl-3-(p-nitrobenzoyl)-1,4-naphthoquinone (synthesized by the synthesis example) represented by the following formula (14),

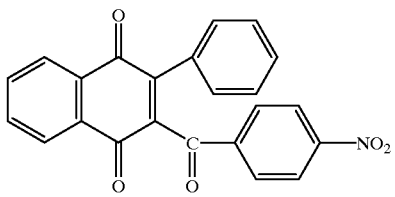

(14)

(ii): 2-phenyl-3-benzoyl-1,4-naphthoquinone represented by the following formula (15),

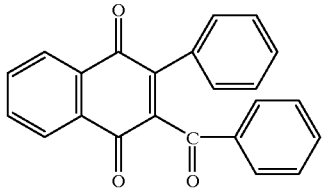

(15)

EXPERIMENTAL EXAMPLE 2

The photosensitive materials prepared in Examples 6 to 9 and Comparative Examples 6 to 9 were evaluated for their repetitive properties according to a method that is described below.

By using a drum sensitivity tester, a voltage was applied to the sample photosensitive materials to electrically charge them up to +700 V ($V_0$), and the electric charge was removed two seconds thereafter. After the process for removing the electric charge was repeated 500 times, the voltage same as the one initially applied was applied, and the charged potential ($V_0'$) at that moment was measured to find the amount of change $\Delta V$ ($V_0'-V_0$) in the charged potential. The results were as shown in Table 2.

TABLE 2

| | $V_0$ [V] | $V_0'$ [V] | $\Delta V$ [V] |
|---|---|---|---|
| Example 6 | 700 | 688 | −12 |
| Example 7 | 700 | 692 | −8 |
| Example 8 | 700 | 695 | −5 |
| Example 9 | 700 | 698 | −2 |
| Comp. Ex. 6 | 700 | 612 | −88 |
| Comp. Ex. 7 | 700 | 625 | −75 |
| Comp. Ex. 8 | 700 | 625 | −75 |
| Comp. Ex. 9 | 700 | 647 | −53 |

I claim:

1. A nitro group-containing naphthoquinone derivative represented by the following general formula

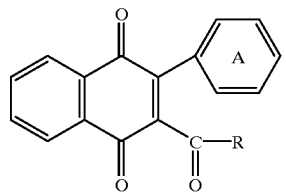

(1)

wherein R is a monovalent hydrocarbon group having a nitro group, and a ring A may be substituted or unsubstituted.

2. A nitro group-containing naphthoquinone derivative according to claim 1, wherein said group R is a monovalent hydrocarbon group selected from the group consisting of an alkyl group having 1 to 10 carbon atoms, an alkenyl group having 2 to 10 carbon atoms, a cycloalkyl group having 3 to 6 carbon atoms, a cycloalkenyl group having 5 to 6 carbon atoms, an aryl group having 6 to 10 carbon atoms and an aralkyl group having 7 to 9 carbon atoms, and in which one to three hydrogen atoms are substituted with nitro groups.

3. A nitro group-containing naphthoquinone derivative according to claim 2, wherein said group R is a p-nitrophenyl group.

* * * * *